(12) United States Patent
Toribio et al.

(10) Patent No.: US 11,304,891 B2
(45) Date of Patent: Apr. 19, 2022

(54) PROCESS FOR EXTRACTING PLANTS

(71) Applicant: CHANEL PARFUMS BEAUTE, Neuilly sur Seine (FR)

(72) Inventors: Alix Toribio, Pantin (FR); David Legangneux, Pantin (FR); Vincent Cocandeau, Pantin (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 0 days.

(21) Appl. No.: 16/883,058

(22) Filed: May 26, 2020

(65) Prior Publication Data

US 2020/0375879 A1 Dec. 3, 2020

(30) Foreign Application Priority Data

May 28, 2019 (EP) .................................... 19305673

(51) Int. Cl.
*A61K 36/00* (2006.01)
*A61K 8/97* (2017.01)
*A61Q 19/08* (2006.01)
*C12N 1/18* (2006.01)
*C12N 5/04* (2006.01)

(52) U.S. Cl.
CPC ................ *A61K 8/97* (2013.01); *A61Q 19/08* (2013.01); *C12N 1/18* (2013.01); *C12N 5/04* (2013.01)

(58) Field of Classification Search
CPC .......................... C12R 2001/865; C12N 1/185
See application file for complete search history.

(56) References Cited

FOREIGN PATENT DOCUMENTS

| CN | 101243897 A | * | 8/2008 |
|---|---|---|---|
| CN | 101243897 A | | 8/2008 |
| FR | 2929852 A1 | | 10/2009 |
| FR | 3026946 A1 | | 4/2016 |
| KR | 100815256 B1 | | 3/2008 |
| KR | 20100006796 A | | 1/2010 |
| KR | 2017026740 A | * | 3/2017 |

OTHER PUBLICATIONS

European Search Report dated Nov. 13, 2019 in corresponding European Application No. 19305673.6; 5 pages.
Lee, Pao-Ju et al., "Analysis of NO—suppressing activity of Strawberry Wine supplemented with ball-milled achenes", Journal of Food Sci Ence and Technology, Springer (India) Private Ltd, India, vol. 55, No. 4, Feb. 2, 2018, pp. 1285-1294.
Mojzer, Brglez Eva et al., "Polyphenols: Extraction Methods, Antioxidative Action, Bioavailability and Anticarcinogenic Effects", Molecules (Basel, Switzerland), Jul. 11, 2016, vol. 21, No. 7, 38 pages.
BulkActives, "Quercetin", BulkActives Ingredients for skin care, Mar. 20, 2015, URL:https://www.bulkactives.com/product/product/quercetin.html (accessed Nov. 12, 2019), 6 pages.
Lallemand Wine, "IOC 18-2007 (TM)", Lallemand Wine catalogue, May 21, 2018, URL:https://catalogapp.lallemandwine.com/uploads/yeasts/docs/253a40560c756452127fa09 a6a24a3b9e0b4592a.pdf (accessed Nov. 13, 2019), 2 pages.
Anonymous, "IOC Divine (TM): Catalogue Lallemand Wine", Lallemand wine catalogue, May 2, 2013, URL:https://www.lallemandwine.com/en/australia/products/catalogue/wine-yeasts/100/ioc/divine/ (accessed Nov. 13, 2019), 2 pages.
Anonymous, "IOC Fizz+ (TM)", Lallemand wine catalogue, May 2, 2013, URL:https://catalogapp.lallemandwine.com/uploads/yeasts/docs/e2926b6a7b4c9708ccc5b9d b0d2517b5e9e760a2.pdf (accessed Nov. 13, 2019), 1 page.

* cited by examiner

*Primary Examiner* — Qiuwen Mi
(74) *Attorney, Agent, or Firm* — Maier & Maier, PLLC

(57) ABSTRACT

A process for the preparation of a plant extract enriched in polyphenols and/or substantially free of simple sugars, as well as the plant extract thus obtained, which may be added to a cosmetic composition. Also, the use of a yeast of the variety *Saccharomyces cerevisiae* var. *bayanus* for the removal of simple sugars in a plant extract.

12 Claims, 1 Drawing Sheet

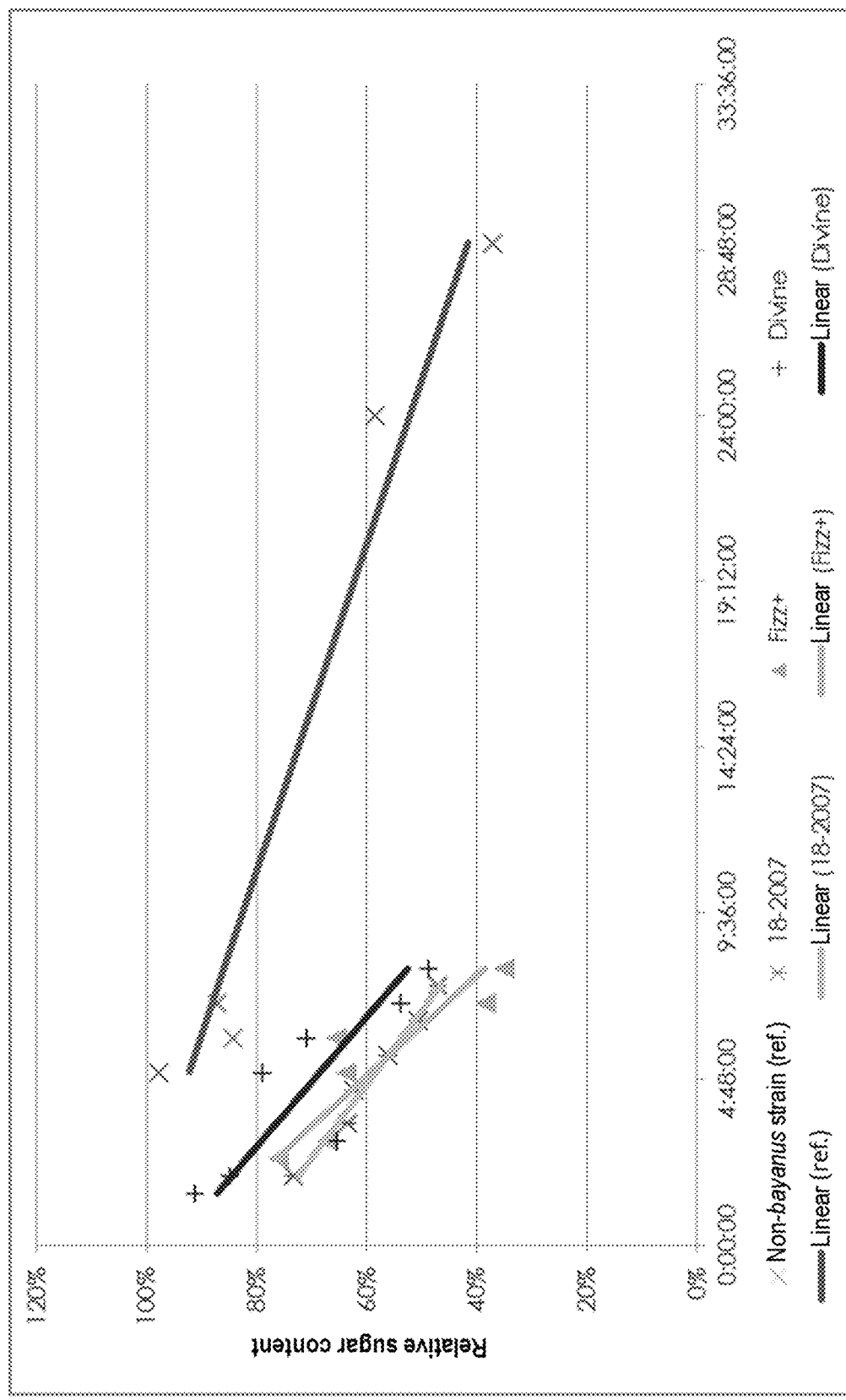

PROCESS FOR EXTRACTING PLANTS

FIELD

The present invention relates to a process for the preparation of a plant extract enriched in polyphenols and/or substantially free of simple sugars. The present invention also relates to a plant extract obtainable by the process according to the invention, and to the cosmetic use of this extract to prevent/reduce skin ageing and/or to hydrate the skin.

BACKGROUND

The skin is mainly made up of three layers, namely, starting from the most superficial, the epidermis, the dermis and the hypodermis.

The epidermis is in particular made up of keratinocytes (the majority), melanocytes (involved in skin pigmentation) and Langerhans cells. Its function is to protect the body from the external environment and to ensure its integrity, and in particular to slow down the penetration of microorganisms or chemical substances, and to prevent the evaporation of water contained in the skin.

To do this, the keratinocytes undergo a continuous process of oriented maturation during which the keratinocytes located in the basal layer of the epidermis form, at the terminal stage of their differentiation, corneocytes, which are dead cells totally keratinized in the form of cornified envelopes consisting of proteins and lipids such as ceramides. During this differentiation process, intercorneocyte epidermal lipids are additionally formed and then organized as bilayers (sheets) in the stratum corneum. Together with the aforementioned cornified envelopes, they participate in the barrier function of the epidermis.

However, the barrier function of the epidermis can be disrupted under certain climatic conditions (under the effect of cold and/or wind, for example), or even under the effect of stress or fatigue, in particular, thus favouring the penetration of allergens, irritants or microorganisms which cause skin dryness likely to generate feelings of discomfort such as tightness or redness, and also to alter the radiance of the complexion and the suppleness of the skin.

To prevent or correct this phenomenon, it is known to apply to the skin cosmetic compositions containing hygroscopic agents, such as sugars or polyols, intended to capture the water present in the skin and thus slow down its evaporation. Generally, these compositions also include active agents that act on one or more biological targets involved, for example, in skin ageing processes.

Due to an ever-increasing willingness of consumers to turn to natural products containing as few synthetic ingredients as possible, and in view of the increasingly heavy regulatory constraints on compounds from the chemical industry, active ingredients from plant extracts are now favoured.

The advantage of plant extracts is that they contain many polyols and particularly polyphenols, whose antioxidant effects are now widely recognized.

However, plant extracts also contain many simple sugars (representing 25 to 75% by weight of conventional extracts) such as glucose, fructose and galactose, which have the effect of impairing the biological activity of plant active ingredients.

In order to reduce their sugar content, plant extracts are generally treated using purification techniques such as the use of resins, activated carbon, cellulose or by distillation. These treatments aim at removing the polar matrix containing simple sugars.

However, these techniques are non-specific and also remove other interesting molecules such as amino acids or organic acids.

Therefore, there is a real need for an extraction process for obtaining plant extracts that contain numerous polyphenols whose moisturizing and antioxidant powers are now widely recognized, but which are also free of simple sugars such as glucose, fructose and galactose which are harmful to the biological activity of the extracts.

SUMMARY

The applicant succeeded in developing a process for the preparation of a plant extract enriched in polyphenols and substantially free of simple sugars. The applicant has in fact demonstrated that it was possible to remove simple sugars and increase the polyphenol content of a plant extract by carrying out a fermentation step of said extract with a yeast of the type *Saccharomyces cerevisiae* var. *bayanus*.

The applicant further demonstrated that the specific use of this variety of yeast made it possible to obtain optimal fermentation kinetics, with rapid and total consumption of the simple sugars contained in the plant extracts.

The present invention therefore relates to a process for the preparation of a plant extract enriched in polyphenols and/or substantially free of simple sugars, comprising a step of fermentation of a plant extract with a yeast belonging to the variety *Saccharomyces cerevisiae* var. *bayanus*.

The present invention also relates to a plant extract obtainable by the process described above. This plant extract has the feature of being substantially free of simple sugars but also of containing high contents of polyphenols such as flavonoids.

The invention further relates, according to another aspect, to a cosmetic composition comprising, in a physiologically acceptable medium, at least one plant extract enriched in polyphenols and/or substantially free of simple sugars as described above.

Finally, the present invention also relates to the use of yeasts of the variety *Saccharomyces cerevisiae* var. *bayanus* for the removal of simple sugars in a plant extract.

BRIEF DESCRIPTION OF THE FIGURE

FIG. 1: Linear regression of total sugars consumed during fermentation for each of the strains studied (*Saccharomyces cerevisiae* reference strain not belonging to the *bayanus* variety [ref], and *Saccharomyces cerevisiae* var. *bayanus* strains 18-2007, Fizz+ and Divine).

DETAILED DESCRIPTION

According to a first aspect, the present invention relates to a process for the preparation of a plant extract enriched in polyphenols and/or substantially free of simple sugars, said process comprising a step of fermentation of a plant extract with a yeast belonging to the variety *Saccharomyces cerevisiae* var. *bayanus*.

Polyphenols are molecules comprising at least two phenolic groups, i.e. comprising at least two benzene rings bearing hydroxyl functions. Particular examples of polyphenols include hydroxybenzoic acids, hydroxycinnamic acids and coumarins, naphthoquinones, stilbenoids or flavonoids. Flavonoids are the most common polyphenols in the plant kingdom, and include in particular flavones, flavonols and dihydroflavonols, flavanones, aurones, chalcones and dihydrochalcones, flavanols, flavanediols, anthocyanidins, and their heterosides. Polyphenols are known for their antioxidant effects, which make them of particularly advantageous anti-ageing active ingredients. In addition, the presence of numerous hydroxyl groups in polyphenols enables the water present in the skin to be captured and thus slows down its evaporation. Polyphenols therefore also have very advantageous moisturizing effects.

An extract "enriched in polyphenols" is used here to refer to an extract comprising from 5.00 to 100% polyphenols by weight, particularly from 5.00 to 85.00% polyphenols by weight, more particularly from 55.00 to 85.00% polyphenols by weight.

According to the present invention, the "simple sugars" are glucose, fructose, galactose and mannose, but also glucose, fructose, galactose and mannose dimers.

In the context of the present invention, an extract "substantially free of simple sugars" is an extract comprising less than 20.00% by weight, particularly less than 10.00% by weight, preferentially less than 5.00% by weight, even more preferably less than 1.00% by weight of simple sugars.

In a particular embodiment, the extract according to the present invention is completely devoid of simple sugars, i.e. it comprises 0% by weight of simple sugars.

The present process comprises a step of fermentation of a plant extract with a yeast belonging to the variety *Saccharomyces cerevisiae* var. *bayanus*. This fermentation step reduces or removes simple sugars contained in a plant extract, but also enriches the polyphenols content of the plant extract.

The applicant demonstrated (see examples below) that the use of a yeast of the variety *Saccharomyces cerevisiae* var. *bayanus* provided optimal fermentation kinetics for plant extracts, and above all much better than those obtained using other varieties of yeast. The *Saccharomyces cerevisiae* var. *bayanus* yeasts particularly reduce the fermentation time of plant extracts, i.e., the time required to consume the sugars in the extract, to less than 24 h. These yeasts therefore quickly and efficiently consume the simple sugars contained in plant extracts.

Yeasts of the variety *Saccharomyces cerevisiae* var. *bayanus* are known and particularly used in the field of oenology. The person skilled in the art knows how to obtain such yeasts to implement the present invention. In a particular embodiment, the yeast *Saccharomyces cerevisiae* var. *bayanus* is selected from among the yeast strains marketed as IOC Fizz+, IOC Divine, IOC 18-2007 or a mixture thereof. All these strains are listed by the Institut Français de la Vigne et du Vin and are easily accessible for the skilled person.

The IOC Fizz+ yeast strain is a mixture of two yeasts deposited at the Institut Pasteur under the number LYCC 6022: LA CLAIRE CGC62 and LYCC 6039: LA CLAIRE SP665.

The IOC Divine strain corresponds to the strain deposited at the Institut Pasteur under the number LYCC 7000, and the strain 18-2007 to the strain deposited at the Institut Pasteur under the number CNCM 1-5320.

The yeast strains according to the present invention may be in dry form, in liquid form or in the form of a yeast cream.

In a particular embodiment, the strain of *Saccharomyces cerevisiae* var. *bayanus* is in dry form.

Typically, the fermentation step is carried out using the strain of *Saccharomyces cerevisiae* var. *bayanus* at between 1 and 5% by mass relative to the solution to be fermented, particularly at between 2 and 3% by mass relative to the solution to be fermented, and more particularly at 2% by mass relative to the solution to be fermented.

The duration of the fermentation step must be sufficient to achieve a simple sugar content of less than 20% by weight, particularly 10% by weight, preferentially less than 5% by weight, even more preferably less than 1% by weight in the plant extract. Typically, the fermentation step is conducted over a period of 1 to 72 hours, particularly 12 to 60 hours, preferably 18 to 48 hours.

In a particular embodiment, the fermentation step can be carried out by means of a leaven. This leaven is prepared from the fermentation of a concentrated plant extract (said plant extract being the same as that used in the process of the invention) with the strain of *Saccharomyces cerevisiae* var. *bayanus*. The plant extract used for the leaven is typically concentrated until a dry matter content of the order of 5 to 30% is obtained.

According to this embodiment, the fermentation step of the process according to the invention is carried out by adding this leaven to the plant extract. The use of a leaven makes it possible to initiate fermentation and thus to improve the kinetics of the fermentation step of the process according to the invention.

Typically, the leaven is prepared by fermenting for about 2 hours at room temperature (or alternatively at 37° C.) a plant extract concentrated to between 5 and 50%, particularly to between 15 and 30% dry matter in water with 10% by weight of dry yeast *Saccharomyces cerevisiae* var. *bayanus*. 1 to 5% by weight of this leaven, preferably 2% by weight of leaven, is added to the plant extract for the fermentation step according to the process of the invention.

The plant extract used according to the process of the invention may be obtained by any extraction process known to the person skilled in the art.

Typically, a process for the preparation of a plant extract comprises the following steps:

a) extraction of the plants with at least one alcoholic solvent and/or water;

b) filtration, for example by sieving, of the mixture obtained in a) in order to remove plant residues, c) optionally, decolorization of the mixture obtained in step b); and d) removal of the solvent and concentration of the extract.

Accordingly, according to an embodiment, the present invention relates to a process for the preparation of a plant extract enriched in polyphenols and/or substantially free of simple sugars comprising the following steps:

a) extraction of the plants with at least one alcoholic solvent and/or water;

b) filtration of the mixture obtained in a), for example by sieving, in order to remove plant residues;

c) optionally, decolorization of the mixture obtained from step b);

d) removal of the solvent, for example by evaporation, and concentration of the extract; and e) fermentation of the extract obtained from step d) with a yeast belonging to the variety *Saccharomyces cerevisiae* var. *bayanus*.

The "plant" used in step a) can be any living thing belonging to the plant kingdom. The plant is a woody terrestrial plant or an herbaceous plant. Preferably, the plant is a phanerogam or "flowering plant". It can, for example, be chosen from lily (*Lilium candidum*), forget-me-not (*Myosotis sylvatica*), elderberry (*Sambucus* sp.), camellia (*Camellia* sp.), primrose (*Primula* sp.), tuberose (*Polianthes tuberosa*), jasmine (*Jasminum grandiflorum*), plantain (*Plantago lan-*

*ceolata*), quince (*Cydonia oblonga*), apricot (*Prunus armeniaca*), or frangipani (*Plumeria* sp.).

The part of the plant extracted in step a) may be the whole plant, or only a part of it, such as the flower, leaves, stems or roots. In a preferred embodiment, the extract is a flower extract.

The plant used in step a) can be in "fresh" form, i.e. used within 48 hours, particularly within 24 hours, and even more particularly within 12 hours of harvest.

The plant used in step a) may also be in dry form. In this case, the fresh plant is dehydrated under gentle conditions, either at room temperature away from light or in a ventilated dryer at a temperature below 35° C. The plant is preferably dried to a dry matter content of more than 80% and preferably more than 85%.

Step a) may further include grinding the plant, typically its flowers and/or leaves, to obtain a particle size of less than 5 cm, preferably less than 2 cm.

The extraction step is carried out with at least one extraction solvent comprising an alcoholic solvent and/or water. The extraction solvent depends on the chosen plant. The typical plant/solvent ratio is 1 to 10 (weight/weight).

The extraction solvent is water and/or an alcoholic solvent. In a particular embodiment, the alcoholic solvent is an alcohol such as ethanol, particularly 96° ethanol.

The extraction solvent may contain 0-100% by volume of water and 0-100% by volume of alcoholic solvent. In a particular embodiment, the extraction solvent comprises 100% water, in another embodiment it comprises 100% ethanol. The extraction solvent may also comprise 50% by volume of water and 50% by volume of ethanol.

In a particular embodiment, the water can be deionized water.

The extraction step lasts at least 1 hour, preferably at least 2 hours, particularly at least 3 hours, and can be repeated once or twice.

As indicated above, the extraction process may include a step in which the mixture from step b) is decolorized. The purpose of this step is to remove pigments present in the extract such as chlorophylls and xanthophylls. The person skilled in the art is familiar with several methods of removing these pigments. Decolorization can, for example, be carried out by bringing the mixture into contact with activated carbon. After decolorization, the mixture is filtered to remove the carbon residue.

Typically, step d) involves concentrating the extract to a dry matter to water ratio in the range of 5 to 30%, preferably 15 to 30%.

The plant extract from step d), i.e. the concentrated plant extract, can be used to prepare the leaven mentioned above.

The process described above may additionally include a step d') between steps d) and e), in which the mixture containing the concentrated extract is finely filtered (typically at 2 μm) to remove fine particles and residual bacteria.

The process may further include a step f), in which the fermented extract is filtered and then diluted to obtain an extract containing 1 to 10% dry matter by weight. This extract may be in the form of a clear and stable aqueous solution.

In a particular embodiment, the process according to the present invention comprises the following steps:
a) A flower powder ground to a fineness of less than 2 cm is extracted twice with ethanol, or water or a mixture of both at 60-75° C. for at least 2 hours;
b) The mixture is filtered down to 4 μm;
c) The resulting mixture is subjected to decolorization by contact with activated carbon for one hour and then undergoes microfiltration down to 1 μm in order to remove the carbon residues;
d) Removal of the extraction solvent by evaporation and concentration of the extract until a dry matter content in water of about 5 to 15% (weight/weight) is reached;
d') The mixture is filtered at 0.2 μm;
e) Fermentation for 24 to 48 hours at 37° C. of the mixture with 2% by weight of a leaven, said leaven having been obtained by concentrating part of the extract obtained before step d) to 30% dry matter in water and adding 10% by weight of dry *Saccharomyces cerevisiae* var. *bayanus* yeasts for a first fermentation for 2 hours at 37° C.;
f) The fermented extract is then filtered at 1 μm and then diluted to obtain an extract containing 1 to 10% dry matter by weight to which a preservative system, based on glycols and/or others, is added.

According to another aspect, the present invention relates to a plant extract obtainable by the process described above, i.e. a plant extract enriched in polyphenols and/or substantially free of simple sugars.

In this context, a subject matter of the invention is therefore a plant extract characterized in that it comprises:
  5.00 to 100.00% of polyphenols by weight, particularly 5.00 to 85.00% of polyphenols by weight, more particularly 55.00 to 85.00% of polyphenols by weight; and/or
  less than 20.00% by weight, particularly less than weight, even more preferably less than 1.00% by weight of simple sugars.

The plant extract according to the invention is used for cosmetic purposes, to moisturize human skin or to protect it from drying out. Thanks to the antioxidant effects of polyphenols, the extract can also be used to combat the signs of ageing such as wrinkles and fine lines, loss of firmness and elasticity due to tissue loss in the epidermis and/or dermis; the loss of radiance due to reduced microcirculation and a slowdown in cell renewal in the epidermis, the appearance of pigmentation spots associated with a malfunction in melanin synthesis, or skin dryness resulting from a reduction in the barrier function of the stratum corneum and a slowdown in epidermal renewal.

Antioxidants are in fact known for their ability to trap free radicals, which are one of the major factors in the acceleration of skin ageing.

The invention also relates to a cosmetic composition comprising a plant extract as described above.

Preferably, said extract is present in the cosmetic or dermatological composition in a proportion of 0.001 to 90% by total weight of the composition, in particular in a proportion of 0.01 to 10%, preferably 0.1 to 10% by total weight of the composition. Said cosmetic or dermatological composition may in particular be suitable for topical application.

Advantageously, said cosmetic or dermatological composition may be in the form of a powder, an emulsion, a microemulsion, a nanoemulsion, a suspension, a solution, a lotion, a cream, an aqueous or hydroalcoholic gel, a foam, a serum, a solution or a dispersion for aerosol, or a dispersion of lipid vesicles.

In the case of an emulsion, it can be a water-in-oil or oil-in-water emulsion.

The cosmetic or dermatological composition according to the invention may also include a solvent chosen according to the various ingredients and the form of administration.

Examples include water (preferably demineralized water), an alcohol such as ethanol, or a diethylene glycol ether such as ethoxydiglycol or diethylene glycol monomethyl ether.

Said cosmetic composition may also comprise, in addition to the extract according to the invention, at least one additive usual in the field, such as for example at least one compound chosen from an emollient or humectant agent, a gelling and/or thickening agent, a surfactant, an oil, an active agent, a dye, a preservative, an antioxidant agent, an active agent, an organic or inorganic powder, a sunscreen and a fragrance.

In particular, said composition may contain:

One or more emollient or humectant agent(s), which may be selected for example from glycerine, glycols, water-soluble silicones such as that sold under the name KF6011 (Shin Etsu) and water-soluble jojoba, such as that sold under the name Resplanta Jojoba (Res Pharma).

Said emollient or humectant agent may be present in the composition at a content in the range of 0 to 30%, preferably to 10% by weight, relative to the total weight of the composition.

One or more gelling and/or thickening agent(s) for the aqueous phase, chosen for example from cellulosic derivatives, gums of plant origin (guar, locust bean, alginates, carrageenans, pectin), of microbial origin (xanthan), clays (laponite), materials identified by the INCI names "ammonium acryloyldimethyltaurate/vp copolymer" and "ammonium acryloyldimethyl-taurate/beheneth-25 methacrylate copolymer" (such as those sold under the names Aristoflex AVC and HMB by Clariant).

Said gelling and/or thickening agent may be present in the composition at a content in the range of 0 to 10% by weight, relative to the total weight of the composition.

One or more surfactant(s), preferably nonionic, present in a content in the range of 0 to 8%, preferably 0.5 to 3% by weight, relative to the total weight of the composition.

One or more room-temperature liquid fats, commonly known as oil(s), volatile or non-volatile, hydrocarbon or silicone, linear, cyclic or branched, for example isododecane, cyclopentadimethylsiloxane, dimethicones, isononyl isononanoate or pentaerythrityl tetraisostearate, preferably in an amount of 0 to about 10%, preferably 0.5 to 5% by weight, relative to the total weight of the composition.

One or more active agent(s), of natural or synthetic origin, having biological activity, for example selected from vitamins, trace elements, allantoin, plant proteins, plant extracts, moisturizing agents, anti-ageing agents, antioxidants, shine enhancers and mixtures thereof. In particular, the active agent is selected from *Vanilla planifolia* fruit water, niacinamide, hyaluronic acid and its derivatives, a yeast extract and mixtures thereof.

One or more water-soluble dye(s) such as, for example, ponceau disodium salt, alizarin green disodium salt, quinoline yellow, amaranth trisodium salt, tartrazine disodium salt, rhodamine monosodium salt, fuchsin or xanthophyll disodium salt, preferably in an amount of 0 to about 2% by weight, relative to the total weight of the composition.

Other additives commonly used in cosmetics may also be present in the composition according to the invention, such as preservatives, antioxidants or fragrances well known in the technical field.

The skilled person is able to choose, from among all these possible additives, both the nature and the amount of those to be added to the composition, so that it retains all its properties.

Finally, according to another aspect, the present invention also relates to the use of yeasts of the variety *Saccharomyces cerevisiae* var. *bayanus* for removing simple sugars in a plant extract.

The invention will now be illustrated by the following non-limiting examples.

EXAMPLES

Example 1—Process for the Extraction of Lilies According to the Present Invention 1) The fresh lily flowers are extracted twice with 96° ethanol at 60° C., for a minimum of 2 hours, the plant/solvent ratio is 1 to 10 (weight/weight);

2) The mixture is sieved at 100 μm in order to remove plant residues, then left to rest overnight and filtered again to 4 μm;

3) The resulting mixture is subjected to decolorization by contact with activated carbon for one hour to remove pigments such as chlorophylls and xanthophylls;

4) The decolorized mixture is separated from the carbon residue by means of microfiltration (to 1 μm);

5) The extraction ethanol is removed by evaporation. The extract is concentrated until a dry matter content in water of about 5% (weight/weight) is reached;

6) The mixture is filtered at 0.2 μm to remove fine particles and residual bacteria;

7) In order to prepare the leaven for the fermentation of the extract, part of the extract obtained before step 6) is concentrated to 30% dry matter in water and then 10% by weight of dry yeast *Saccharomyces cerevisiae* var. *bayanus* is added. The mixture is stirred for 2 hours at 37° C. This mixture constitutes the leaven.

8) 2% of leaven by weight is added to the mixture from step 6)

9) After 24 to 48 hours of fermentation at 37° C. with stirring and in the dark, the fermented extract is left to settle overnight to remove the gas bubbles formed.

10) The fermented extract is then filtered at 1 μm, then diluted to obtain an extract containing 1% dry matter. 0.7% phenoxyethanol or 20% 1,3-propanediol is added for better preservation and the whole is filtered at 0.2 μm.

The contents of lily flower extract are given in Table 1 below.

TABLE 1

Composition of a lily extract according to the invention
Lily flowers (*Lilium candidum*)

| Molecular family | Molecules | Conventional dry extract | Conventional extract diluted to 1% | Dry fermented extract | Fermented extract diluted to 1% |
|---|---|---|---|---|---|
| Saccharides | Fructose, Glucose, Sucrose | 58.00% | 0.58% | 0.00% | 0.00% |
| Nitrogenous and other | Lilidine glucoside, Glucopyranosyl glycerol, Hopantenic acid | 15.30% | 0.15% | 48.60% | 0.48% |
| Flavonoids and other polyphenols | 1 di and tri-glucosides, Quercetin di-glucosides, Helionosides A, Regaloside A | 3.50% | 0.03% | 9.00% | 0.09% |
| Lipids | Fatty acids C16:0, C18:0, C18:1, C18:2, C18:3 | 3.00% | 0.03% | 0.00% | 0.00% |
| Others | Others | 19.70% | 0.20% | 42.40% | 0.42% |

As demonstrated above, the process according to the present invention completely removes simple sugars from an extract of lily flowers. The process according to the invention greatly increases the polyphenol content of the extract.

Example 2—the Fermentation Kinetics of the Dry Yeasts of *Saccharomyces cerevisiae* Var. *bayanus* Fizz+, Divine and 18-2007 Allow Optimal Fermentation of Flower Extracts A fermentation kinetics study was conducted to determine which yeasts are more efficient.

In general, the fermentation of flower extracts can be subdivided into three successive steps (M. H. Akin, "*Evolution du pH pendant la fermentation alcoolique de moûts de raisins: modélisation et interprétation métabolique*" ["Change in pH during alcoholic fermentation of grape musts: modelling and metabolic interpretation"] (2008) 136):

step 1: hydrolysis of sucrose to fructose and glucose (lasts between 15 and 30 minutes)

step 2: start consumption of glucose (lasts up to 5 hours)

step 3: start consumption of fructose and consumption of other monosaccharides (varies by strain)

In order to select the yeast strain allowing for optimal fermentation, we evaluated the consumption rate of total sugars in step 3 from the lily extract with various commercial yeast strains.

The slopes were obtained by linear regression of the relative contents of total sugars. The lower the slope, the greater the kinetics (FIG. 1).

TABLE 2

Comparison of total sugar consumption rates for different yeast strains.

| | Speed of consumption of total sugars | Slope | $R^2$ |
|---|---|---|---|
| Reference strain *Saccharomyces cerevisiae* non bayanus (ref.) | 2.1%/h | −0.5 | 0.94 |
| 18-2007 | 4.7%/h | −1.13 | 0.98 |
| Fizz+ | 6.8%/h | −1.64 | 0.79 |
| Divine | 5.3%/h | −1.28 | 0.73 |

Thus, the results of FIG. 1 and Table 2 show that the Fizz+, Divine, 18-2007 and reference (ref.) strains consumed 6.8%, 5.3%, 4.7% and 2.1% of the total sugars of the lily flower extract per hour, respectively.

This comparison then makes it possible to classify the 4 strains according to their speed of sugar consumption in the following way: Fizz+>Divine >18-2007 > reference non-bayanus.

The reference strain, which does not belong to the variety *Saccharomyces cerevisiae* var. *bayanus*, consumes total sugars two to three times slower than the strains Fizz+, Divine and 18-2007, which belong to the variety *Saccharomyces cerevisiae* var. *bayanus*.

The *Saccharomyces cerevisiae* var. *bayanus* yeasts allow for optimal fermentation kinetics of plant extracts.

Example 3: Cosmetic Composition

The following composition can be prepared in a traditional way for the skilled person. The amounts indicated below are expressed in weight percentages. Ingredients in capital letters are identified in accordance with the INCI designation.

Oil-in-Water Emulsion

| INCI/TRADE NAME (SUPPLIER) | (% W/W) |
|---|---|
| Jojoba esters | 1-10 |
| *Camellia* seed oil | 1-10 |
| *Butyrospermum Parkii* Butter (LIPEX SHEA) | 1-10 |
| *Butyrospermum parkii* butter (LIPEX SHEASOFT) | 1-10 |
| Shea Butter Ethyl Esters (LIPEX SHEALIGHT) | 1-10 |
| *Butyrospermum parkii* butter extract (LIPEX SHEA TRIS) | 1-10 |
| PHYTOSQUALAN | 0.5-7 |
| Cetyl dimethicone (ABIL WAX 9801) | 0.1-7 |
| Isostearyl isostearate (CRODAMOL ISIS-LQ) | 1-5 |
| Cetyl alcohol & glyceryl stearate & peg-75 stearate & ceteth-20 & steareth-20 (EMULIUM DELTA) | 1-5 |
| Sodium polyacrylate (COVACRYL MV 60) | 1-5 |
| Silica & lauroyl lysine (AMILON) | 0.1-10 |
| Sodium hyaluronate | 0.01-3 |
| Glycerine | 1-30 |
| Polyquaternium-51 | 1-10 |
| Extract according to the invention | 0.001-10 |
| Adenosine | 0.1-0.5 |
| Niacinamide | 0.1-5 |
| Palmitoyl Tripeptide-1 & Palmitoyl Tetrapeptide-7 | 1-5 |
| Secale Cereale (Rye) Seed Extract | 1-5 |
| Ascorbyl glucoside | 0.001-5 |
| Glycols (Caprylyl Glycol and/or Pentylene Glycol and/or Butylene Glycol and/or propanediol) | 0.1-10 |
| Water | Qs 100 |

The invention claimed is:

1. A process for the preparation of a cosmetic flower extract enriched in polyphenols and/or substantially free of simple sugars, comprising the steps of:
    fermenting a flower extract having a dry matter content in water in a range of 5% to 30% (weight/weight) with a yeast belonging to the variety *Saccharomyces cerevisiae* var. *bayanus*.

2. The process according to claim 1 comprising, prior to the fermentation step, the preparation of the flower extract by means of the following steps:
    a) extracting at least one flower with at least one alcoholic solvent and/or water to obtain a mixture;
    b) filtering the mixture obtained in a) in order to remove plant residues to obtain a mixture without plant residues;
    c) optionally, decolorizing the mixture obtained in step b); and
    d) removal of the solvent and concentration of the extract obtained, the extract having dry matter content in water in a range of 5% to 30% (weight/weight).

3. The process according to claim 1, wherein the flower is a flower of *Lilium candidum, Myosotis sylvatica, Sambucus* sp., *Camellia* sp., *Primula* sp., *Polianthes tuberosa, Jasminum grandiflorum, Plantago lanceolata, Cydonia oblonga, Prunus armeniaca* or *Plumeria* sp.

4. The process according to claim 1, wherein the step of fermenting is carried out by means of a leaven prepared from the fermentation of a concentrated flower extract with the strain of *Saccharomyces cerevisiae* var. *bayanus*.

5. The process according to claim 1, wherein the fermented flower extract comprises 5.00 to 100.00% of polyphenols by weight.

6. The process according to claim 5, wherein the fermented flower extract comprises 5.00 to 85.00% of polyphenols by weight.

7. The process according to claim 6, wherein the fermented flower extract comprises 55.00 to 85.00% of polyphenols by weight.

8. The process according to claim 1, wherein the fermented flower extract comprises less than 20.00% by weight of simple sugars.

9. The process according to claim 8, wherein the fermented flower extract comprises less than 5.00% by weight of simple sugars.

10. The process according to claim 9, wherein the fermented flower extract comprises less than 1.00% by weight of simple sugars.

11. The process according to claim 1, wherein the fermented flower extract is free of simple sugars.

12. The process according to claim 1, comprising, prior to the fermentation step, the preparation of the flower extract by means of the following steps:
    a) extracting at least one flower with at least one alcoholic solvent and/or water to obtain a mixture;
    b) filtering the mixture obtained in a) in order to remove plant residues to obtain a mixture without plant residues;
    c) decolorizing the mixture obtained in step b) by contacting with activated carbon; and
    d) removal of the solvent and concentration of the extract obtained, the extract having dry matter content in water in a range of 5% to 30% (weight/weight).

\* \* \* \* \*